United States Patent
Baiko

(10) Patent No.: US 11,213,648 B2
(45) Date of Patent: Jan. 4, 2022

(54) CUSHION MEMBER WITH ENGAGING ELEMENT

(71) Applicant: KONINKLIJKE PHILIPS N.V., Eindhoven (NL)

(72) Inventor: Robert William Baiko, Pittsburgh, PA (US)

(73) Assignee: Koninklijke Philips N.V., Eindhoven (NL)

( * ) Notice: Subject to any disclaimer, the term of this patent is extended or adjusted under 35 U.S.C. 154(b) by 271 days.

(21) Appl. No.: 16/467,544

(22) PCT Filed: Dec. 12, 2017

(86) PCT No.: PCT/EP2017/082297
§ 371 (c)(1),
(2) Date: Jun. 7, 2019

(87) PCT Pub. No.: WO2018/108847
PCT Pub. Date: Jun. 21, 2018

(65) Prior Publication Data
US 2020/0001033 A1    Jan. 2, 2020

Related U.S. Application Data

(60) Provisional application No. 62/433,284, filed on Dec. 13, 2016.

(51) Int. Cl.
*A61M 16/06* (2006.01)

(52) U.S. Cl.
CPC .............................. *A61M 16/0622* (2014.02)

(58) Field of Classification Search
CPC .................... A61M 16/0616; A61M 16/0622
See application file for complete search history.

(56) References Cited

U.S. PATENT DOCUMENTS

| | | | | |
|---|---|---|---|---|
| 3,330,273 A | * | 7/1967 | Bennett | A62B 18/025 128/206.26 |
| 5,349,949 A | * | 9/1994 | Schegerin | A62B 18/08 128/201.24 |
| 8,485,192 B2 | * | 7/2013 | Davidson | A61M 16/0622 128/206.24 |
| 8,596,273 B2 | | 12/2013 | Burz et al. | |

(Continued)

OTHER PUBLICATIONS

International Search Report—PCT/EP2017/082297 filed Dec. 12, 2017.

*Primary Examiner* — Valerie L Woodward
(74) *Attorney, Agent, or Firm* — Michael W. Haas

(57) ABSTRACT

A cushion member (10) is for use in a pressure support system (2) for delivering a flow of breathing gas to an airway of a patient. The cushion member includes an annular body (12) comprising a first end (14) and a second end (16) disposed opposite the first end, the body defining a passage (18) therethrough; a sealing portion (20) extending from the second end of the body into the passage, the sealing portion having an outer surface (21) structured to sealingly engage about the airway of the patient and an inner surface (23) disposed opposite the outer surface; and a support portion (22,24) extending from the second end of the body into the passage and terminating at a distal end (26,28). The distal end of the support portion engages a portion of the body at or about the second end.

13 Claims, 7 Drawing Sheets

(56) References Cited

U.S. PATENT DOCUMENTS

| | | |
|---|---|---|
| 9,132,255 B2 | 9/2015 | Skipper et al. |
| 9,981,102 B2 | 5/2018 | Lee |
| 2007/0221227 A1 | 9/2007 | Ho |
| 2008/0006277 A1* | 1/2008 | Worboys ............... A61M 16/06 128/207.13 |
| 2008/0110464 A1* | 5/2008 | Davidson .............. A61M 16/06 128/206.26 |
| 2010/0006100 A1 | 1/2010 | Eifler et al. |
| 2014/0326246 A1 | 11/2014 | Chodkowski et al. |
| 2015/0144140 A1 | 5/2015 | Eury |
| 2018/0256843 A1* | 9/2018 | Eves ..................... A61M 16/06 |
| 2019/0111227 A1 | 4/2019 | Lee et al. |

* cited by examiner

CUSHION MEMBER WITH ENGAGING ELEMENT

CROSS-REFERENCE TO RELATED APPLICATIONS

This application claims the priority benefit under 35 U.S.C. § 371 of International Patent Application No. PCT/EP2017/082297, filed on Dec. 12, 2017, which claims the priority benefit of U.S. Provisional Patent Application No. 62/433,284, filed on Dec. 13, 2016, the contents of which are herein incorporated by reference.

BACKGROUND OF THE INVENTION

1. Field of the Invention

The present invention relates to cushion members such as for example, cushion members for patient interface devices. The present invention also relates to pressure support systems including cushion members.

2. Description of the Related Art

Many individuals suffer from disordered breathing during sleep. Sleep apnea is a common example of such sleep disordered breathing suffered by millions of people throughout the world. One type of sleep apnea is obstructive sleep apnea (OSA), which is a condition in which sleep is repeatedly interrupted by an inability to breathe due to an obstruction of the airway; typically the upper airway or pharyngeal area. Obstruction of the airway is generally believed to be due, at least in part, to a general relaxation of the muscles which stabilize the upper airway segment, thereby allowing the tissues to collapse the airway. Another type of sleep apnea syndrome is a central apnea, which is a cessation of respiration due to the absence of respiratory signals from the brain's respiratory center. An apnea condition, whether obstructive, central, or mixed, which is a combination of obstructive and central, is defined as the complete or near cessation of breathing, for example a 90% or greater reduction in peak respiratory air-flow.

Those afflicted with sleep apnea experience sleep fragmentation and complete or nearly complete cessation of ventilation intermittently during sleep with potentially severe degrees of oxyhemoglobin desaturation. These symptoms may be translated clinically into extreme daytime sleepiness, cardiac arrhythmias, pulmonary-artery hypertension, congestive heart failure and/or cognitive dysfunction. Other consequences of sleep apnea include right ventricular dysfunction, carbon dioxide retention during wakefulness, as well as during sleep, and continuous reduced arterial oxygen tension. Sleep apnea sufferers may be at risk for excessive mortality from these factors as well as by an elevated risk for accidents while driving and/or operating potentially dangerous equipment.

Even if a patient does not suffer from a complete or nearly complete obstruction of the airway, it is also known that adverse effects, such as arousals from sleep, can occur where there is only a partial obstruction of the airway. Partial obstruction of the airway typically results in shallow breathing referred to as a hypopnea. A hypopnea is typically defined as a 50% or greater reduction in the peak respiratory air-flow. Other types of sleep disordered breathing include, without limitation, upper airway resistance syndrome (UARS) and vibration of the airway, such as vibration of the pharyngeal wall, commonly referred to as snoring.

It is well known to treat sleep disordered breathing by applying a continuous positive air pressure (CPAP) to the patient's airway. This positive pressure effectively "splints" the airway, thereby maintaining an open passage to the lungs. It is also known to provide a positive pressure therapy in which the pressure of gas delivered to the patient varies with the patient's breathing cycle, or varies with the patient's breathing effort, to increase the comfort to the patient. This pressure support technique is referred to as bi-level pressure support, in which the inspiratory positive airway pressure (IPAP) delivered to the patient is higher than the expiratory positive airway pressure (EPAP). It is further known to provide a positive pressure therapy in which the pressure is automatically adjusted based on the detected conditions of the patient, such as whether the patient is experiencing an apnea and/or hypopnea. This pressure support technique is referred to as an auto-titration type of pressure support, because the pressure support device seeks to provide a pressure to the patient that is only as high as necessary to treat the disordered breathing.

Pressure support therapies as just described involve the placement of a patient interface device including a mask component having a soft, flexible sealing cushion member on the face of the patient. The mask component may be, without limitation, a nasal mask that covers the patient's nose, a nasal/oral mask that covers the patient's nose and mouth, or a full face mask that covers the patient's face. Such patient interface devices may also employ other patient contacting components, such as forehead supports, cheek pads and chin pads. The patient interface device is typically secured to the patient's head by a headgear component. The patient interface device is connected to a gas delivery tube or conduit and interfaces the pressure support device with the airway of the patient, so that a flow of breathing gas can be delivered from the pressure/flow generating device to the airway of the patient.

One drawback of known patient interface devices is on the ability of the cushion member to properly seal with the face of the patient. Most cushion members are structured with a dual flap sealing system. More specifically, one flap is structured as a support flap, and one flap is structured as a sealing flap. Many of these dual flap systems collapse in use and experience thus provide support only at the transition location at the edge of the sealing flap wall. This provides a relatively localized force (i.e., higher pressure at the point of contact) which can often result in undesirable pressure points, red marks, and a lack of seal. Furthermore, known support flaps typically do a poor job at providing supporting force in a direction perpendicular to the flap wall.

SUMMARY OF THE INVENTION

Accordingly, it is an object of the present invention to provide an improved cushion member and pressure support system including the same.

In accordance with one aspect of the disclosed concept, a cushion member is provided for use in a pressure support system for delivering a flow of breathing gas to an airway of a patient. The cushion member includes an annular body comprising a first end and a second end disposed opposite the first end, the body defining a passage therethrough; a sealing portion extending from the second end of the body into the passage, the sealing portion having an outer surface structured to sealingly engage about the airway of the patient and an inner surface disposed opposite the outer surface; and a support portion extending from the second end of the body into the passage and terminating at a distal end. The distal end of the support portion engages a portion of the body at or about the second end.

As another aspect of the disclosed concept, a cushion member is provided for use in a pressure support system for delivering a flow of breathing gas to an airway of a patient. The cushion member includes an annular body comprising a first end and a second end disposed opposite the first end, the body defining a passage therethrough; a sealing portion extending from the second end of the body into the passage, the sealing portion having an outer surface structured to sealingly engage about the airway of the patient and an inner surface disposed opposite the outer surface; and a support portion extending from the second end of the body into the passage and terminating at a distal end. The support portion is movable between a first position corresponding to disengagement between the distal end of the support portion and the body, and a second position corresponding to engagement between the distal end of the support portion and a portion of the body at or about the second end.

As another aspect of the disclosed concept, a pressure support system including a gas flow generator, a conduit coupled to the gas flow generator, and either one of the aforementioned cushion members is provided.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

Figure 1:
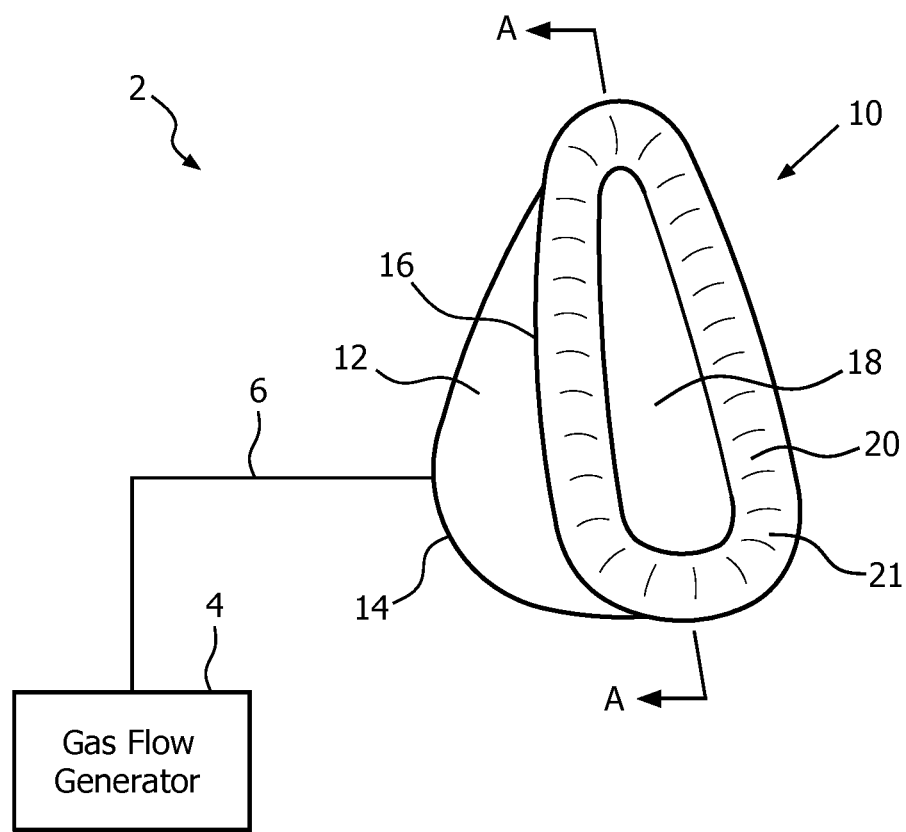
FIG. 1 is a simplified, partially schematic view of a pressure support system and cushion member for the same, in accordance with one non-limiting embodiment of the disclosed concept.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, left, right, upper, lower, front, back, on top of, and derivatives thereof, relate to the orientation of the elements shown in the drawings and are not limiting upon the claims unless expressly recited therein.

FIG. 1 is a simplified, partially schematic view of a pressure support system 2, in accordance with one non-limiting embodiment of the disclosed concept. Pressure support system 2 includes, among other components, a gas flow generator 4 (shown in simplified form), a conduit (e.g., without limitation, hose 6, shown in simplified form), and a novel cushion member 10. Gas flow generator 4 is structured to generate a flow of breathing gas to be delivered to an airway of a patient. Hose 6 fluidly couples gas flow generator 4 to cushion member 10 via a suitable frame member (not shown) and/or fluid coupling conduit (not shown) in order to allow pressure support therapy to be delivered to an airway of a patient. Cushion member 10 includes an annular body 12 having a first end 14 and a second end 16 located opposite first end 14. First end 14 is indirectly coupled to hose 6. Body 12 defines a passage 18 therethrough. Cushion member 10 further includes a sealing portion 20 extending radially inwardly from second end 16 of body 12 into passage 18. Sealing portion 20 has an outer surface 21 structured to sealingly engage about the airway of the patient and an inner surface 23 (shown in FIGS. 2-4) located opposite outer surface 21.

Figure 2:
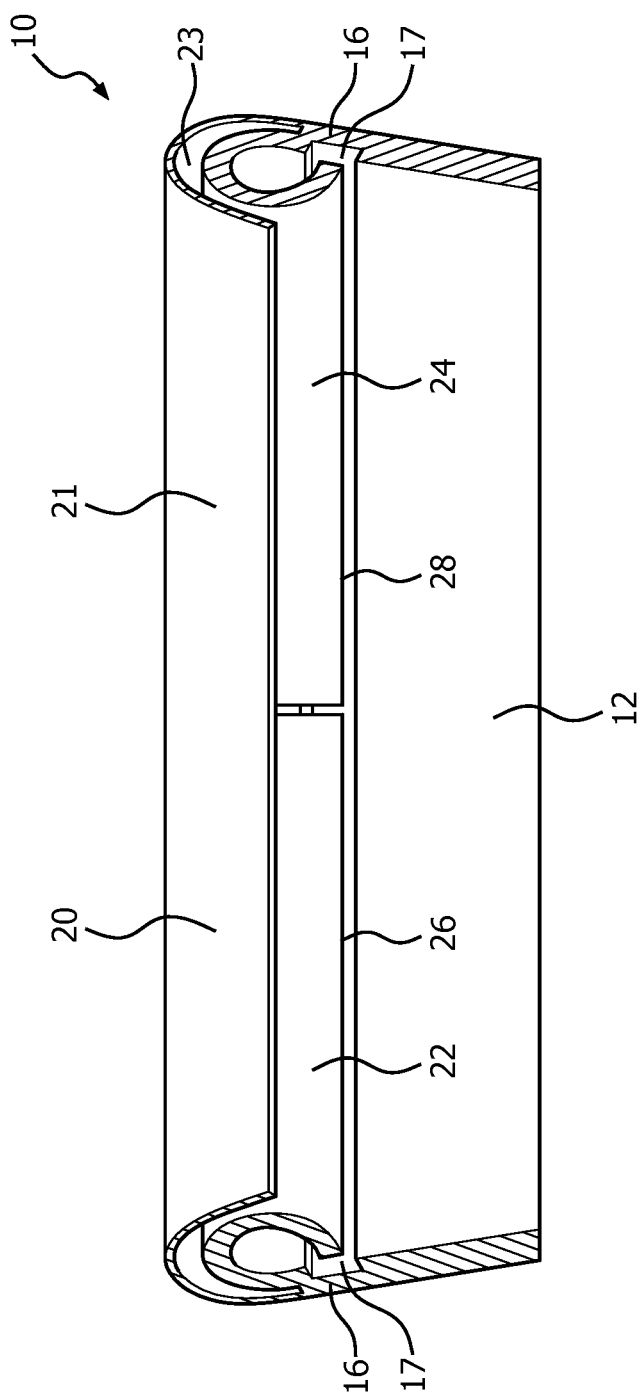
FIG. 2 is a section view of a portion of the cushion member of FIG. 1, taken along line A-A of FIG. 1.

FIG. 2 is a section view of a portion of cushion member 10. As shown, cushion member 10 further includes a number of support portions 22,24 extending radially inwardly from second end 16 of body 12 into passage 18 (FIG. 1). Support portions 22,24 are spaced from and located adjacent one another. That is, support portions 22,24 in the instant exemplary embodiment are not connected with one another. In this manner, when cushion member 10 is donned by a patient, support portions 22,24 will have space in which to flex circumferentially, rather than potentially being constrained, as would be the case with a continuous support portion. Support portions 22,24 each terminate at a respective distal end 26,28 located inboard of second end 16 of body 12. Furthermore, second end 16 of body 12 includes an annular-shaped groove 17 defined in body 12.

Figure 3:
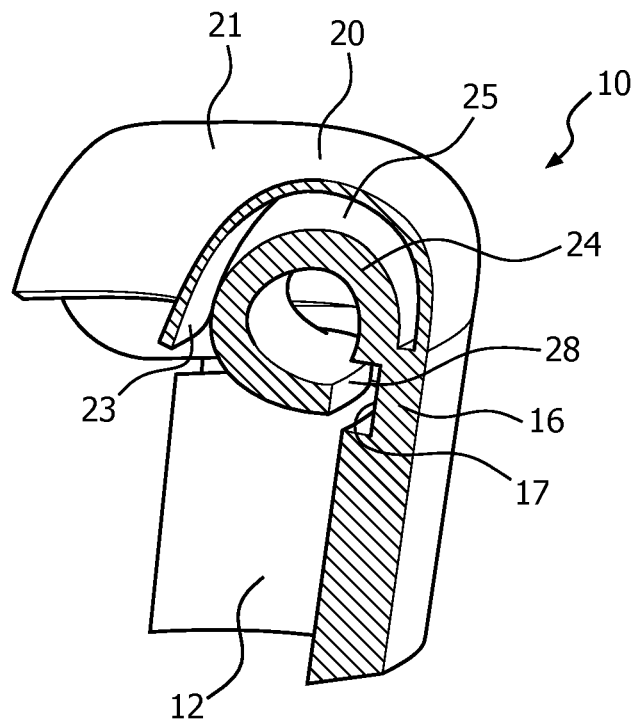
FIG. 3 is a side elevation view of a portion of the section view of FIG. 2, shown with a distal end spaced from a groove.

FIG. 3 shows a side elevation view of a portion of cushion member 10 depicted in FIG. 2. As shown, distal end 28 of support portion 24 is spaced from second end 16 of body 12. This position corresponds to cushion member 10 not being donned by a patient.

Figure 4:
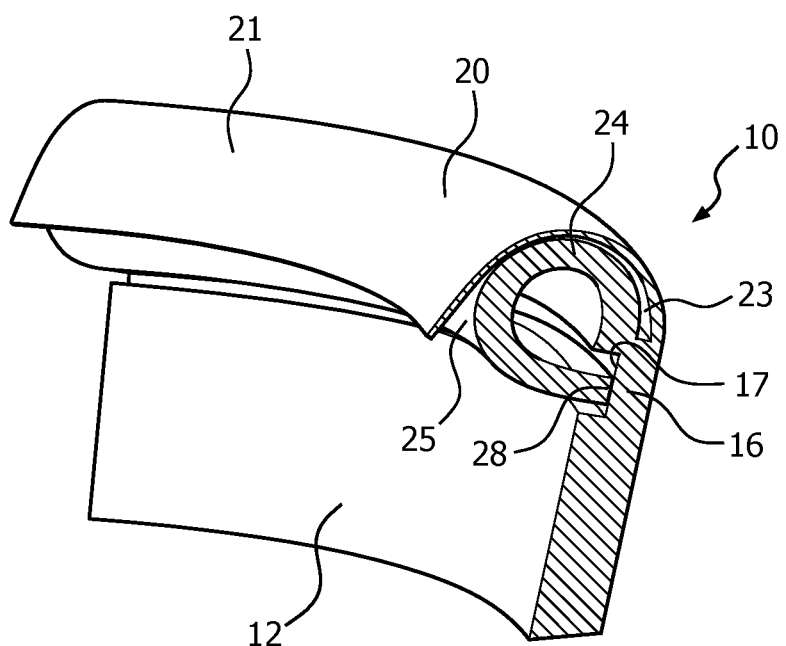
FIG. 4 is another side elevation view of a portion of the section view of FIG. 2, shown with the distal end engaging the groove.

FIG. 4 shows another side elevation view of the portion of cushion member 10 depicted in FIG. 2. As shown, distal end 28 of support portion 24 engages and is interlocked with a portion of body 12 at or about second end 16. In one example embodiment, distal end 28 is engaged with groove 17 to provide a relatively secure connection. In other words, distal end 28 may be interlocked with, reliably maintained on, connected with, or fastened to, groove 17 in the position of FIG. 4. However, it will be appreciated that distal end 28 may be engaged with second end 16, or a suitable alternative second end (not shown), in any suitable alternative manner (e.g., without limitation, being adhesively connected). It will also be appreciated that support portion 24 may provide support until a certain limit (i.e., a certain tightness between cushion member 10 and the face of the patient) is reached, at which point support portion 24 will collapse so as to avoid excessive contact pressure. In contrast to FIG. 3, the position of FIG. 4 corresponds to cushion member 10 being donned by a patient, or engaging the face of a patient such as, for example and without limitation, when pressure support therapy is being delivered to the patient. Accordingly, support portion 24 is movable between a first position (FIG. 3) corresponding to disengagement between distal end 28 of support portion 24 and body 12, and a second position (FIG. 4) corresponding to engagement between distal end 28 of support portion 24 and a portion of body 12 at or about second end 16.

As shown in FIG. 4, when distal end 28 is engaged with groove 17, support portion 24 is generally tubular-shaped, and inner surface 23 of sealing portion 20 engages an outer surface 25 of support portion 24. In this manner, support portion 24 (e.g., and also support portion 22 (FIG. 2) by virtue of distal end 26 being engaged with second end 16) is advantageously able to provide improved support to sealing portion 20. That is, rather than support portions 22,24 collapsing when sealing portion 20 is pressed into them, as would be the case with a prior art support portion (not shown), support portions 22,24 are uniquely structured to provide novel support to sealing portion 20. For example, inner surface 23 of sealing portion 20 engages outer surface 25, and support portions 22,24 remain generally tubular-shaped when distal ends 26,28 engage groove 17. Thus, the pressure exerted on the face of the patient by sealing portion 20 is advantageously reduced, as there will be a greater surface area for sealing portion 20 to engage the face of the patient. Stated differently, the support provided to sealing portion 20 is such that the force exerted on the face of the patient by sealing portion 20 spans a multitude of angles, rather than being a singularly directed localized force, as is the case with prior art cushion members (not shown). This translates into a reduction in red marks and an improved seal when pressure support therapy is delivered to the patient.

Figure 5A:
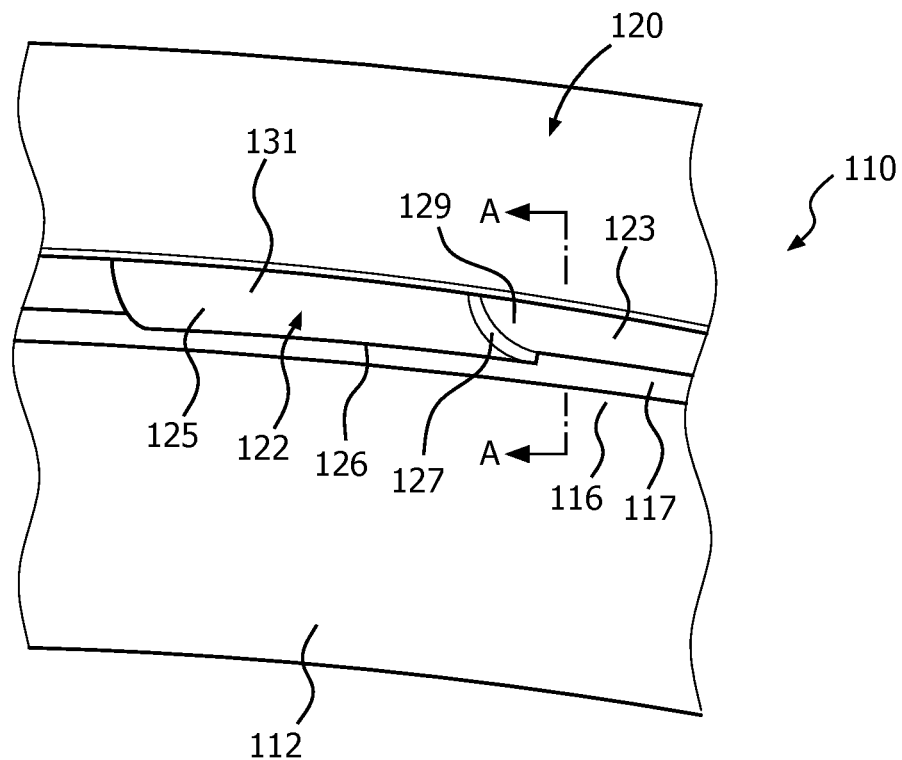
FIG. 5A is an enlarged view of a portion of another cushion member, in accordance with another non-limiting embodiment of the disclosed concept.

FIG. 5A is an enlarged view of a portion of another cushion member 110 that may be substituted into pressure support system 2 (FIG. 1) in place of cushion member 10 (FIG. 1), in accordance with another non-limiting embodiment of the disclosed concept. Cushion member 110 includes a sealing portion 120 and a support portion 122 that each extend from a second end 116 of a body 112. Support portion 122 terminates at a distal end 126, and second end 116 of body 112 has an annular-shaped groove 117. In one example embodiment, distal end 126 is engaged with groove 117 to provide substantially the same advantages as cushion member 10, discussed above. As shown in FIG. 5A, support portion 122 includes a first circumferential portion 123 and a second circumferential portion 125 extending from first circumferential portion 123. First circumferential portion 123 and second circumferential portion each extend radially inwardly from second end 116 into a corresponding passage of cushion member 110.

Figure 5B:
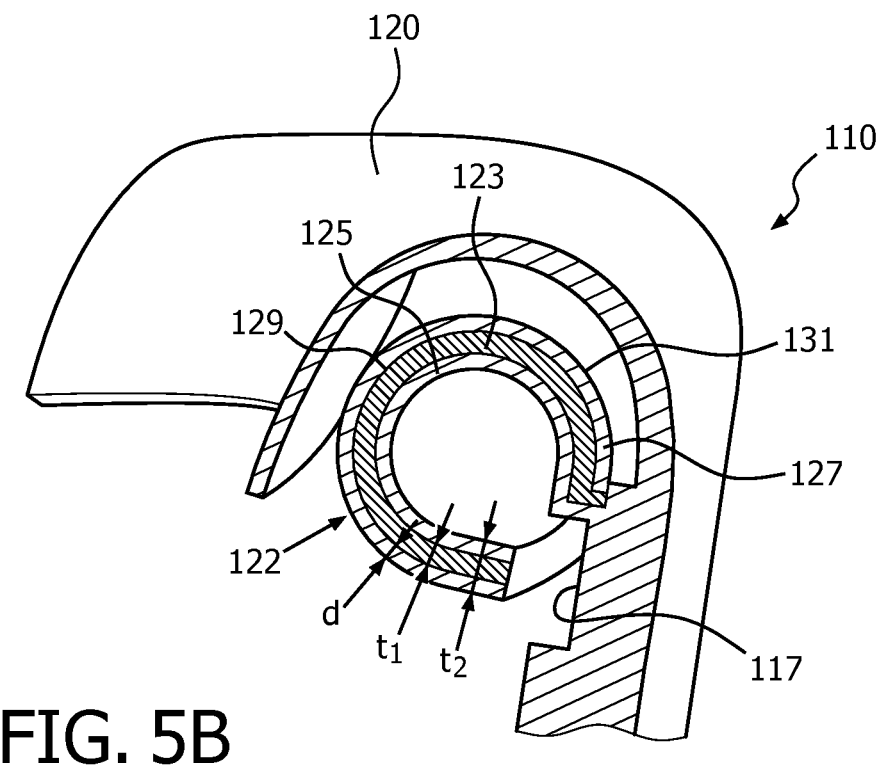
FIG. 5B is a section view of a portion of the cushion member of FIG. 5A, taken along line A-A of FIG. 5A.

As shown in FIG. 5B, first circumferential portion 123 has a first thickness $t_1$ and second circumferential portion 125 has a second thickness $t_2$ greater than first thickness $t_1$ of first circumferential portion 123. In this manner, certain regions of sealing portion 120 can advantageously receive greater amounts of support and be more stiff than others. For example, the portion of sealing portion 120 engaging second circumferential portion 125 will be more supported and will feel more stiff to a patient than the portion of sealing portion 120 engaging first circumferential portion 123. This is advantageous because certain areas of sealing portions of cushion members are known to generate more redmarks than others (e.g., without limitation, for full face masks, nose bridge regions commonly generate redmarks on the face of the patient during therapy). As such, the nose bridge region of the support portion under a sealing portion can advantageously be made more stiff, in the manner discussed herein, to remedy this drawback.

Furthermore, as shown in FIG. 5A, the first circumferential portion 123 has a first outer surface 129 and second circumferential portion 125 has a second outer surface 131. Support portion 122 also has a transition surface 127 extending from and being located perpendicular to first outer surface 129 and second outer surface 131 such that first outer surface 129 is offset a distance d (shown in FIG. 5B) from second outer surface 131. In this manner, a sharp transition between circumferential portions of different thickness is advantageously able to be achieved.

Figure 6A:
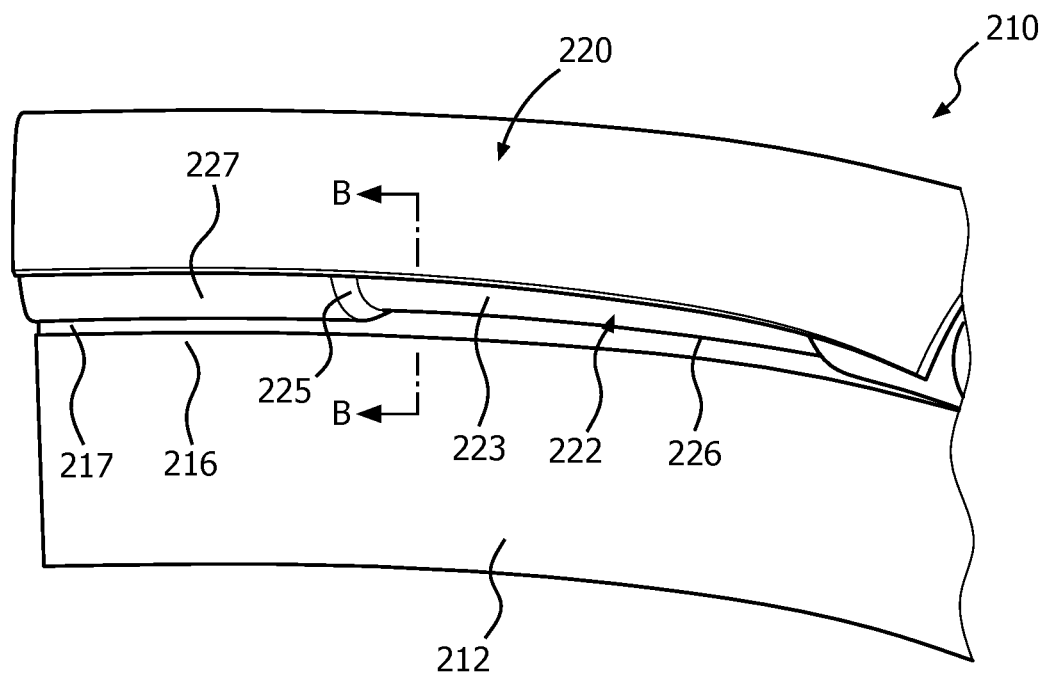
FIG. 6A is an enlarged view of a portion of another cushion member, in accordance with another non-limiting embodiment of the disclosed concept.

FIG. 6A is an enlarged view of a portion of another cushion member 210 that may be substituted into pressure support system 2 (FIG. 1) in place of cushion member 10 (FIG. 1), in accordance with another non-limiting embodiment of the disclosed concept. Cushion member 210 includes a sealing portion 220 and a support portion 222 that each extend from a second end 216 of a body 212. Support portion 222 terminates at a distal end 226, and second end 216 has an annular-shaped groove 217. In one example embodiment, distal end 226 is engaged with groove 217 to provide substantially the same advantages as cushion members 10,110, discussed above. As shown in FIG. 6A, support portion 222 includes a first circumferential portion 223, a second circumferential portion 225 extending from first circumferential portion 223, and a third circumferential portion 227 extending from second circumferential portion 225 away from first circumferential portion 223. First, second, and third circumferential portions 223,225,227 each extend radially inwardly from second end 216 into a corresponding passage of cushion member 210.

Figure 6B:
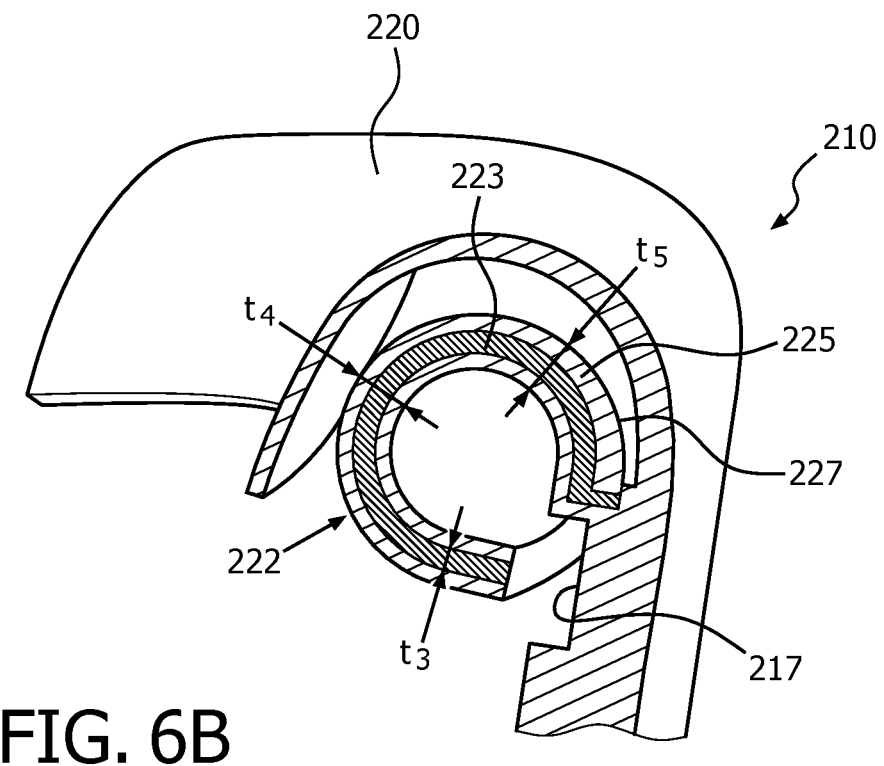
FIG. 6B is a section view of a portion of the cushion member of FIG. 6A, taken along line B-B of FIG. 6A.

As shown in FIG. 6B, first circumferential portion 223 has a first thickness $t_3$, second circumferential portion 225 has a second thickness (i.e., a second thickness $t_4$ of a portion of second circumferential portion 225 is shown in FIG. 6B), and third circumferential portion 227 has a third thickness $t_5$. Second thickness $t_4$ is greater than first thickness $t_3$, and third thickness $t_5$ is greater than first thickness $t_3$ and second thickness $t_4$. More specifically, second circumferential portion 225 provides a transition region in which the thickness of support portion can gradually increase from first thickness $t_3$ of first circumferential portion 223 to third thickness is of third circumferential portion 227. In this manner, a gradual transition between circumferential portions of different thickness is advantageously able to be achieved.

Figure 7A:
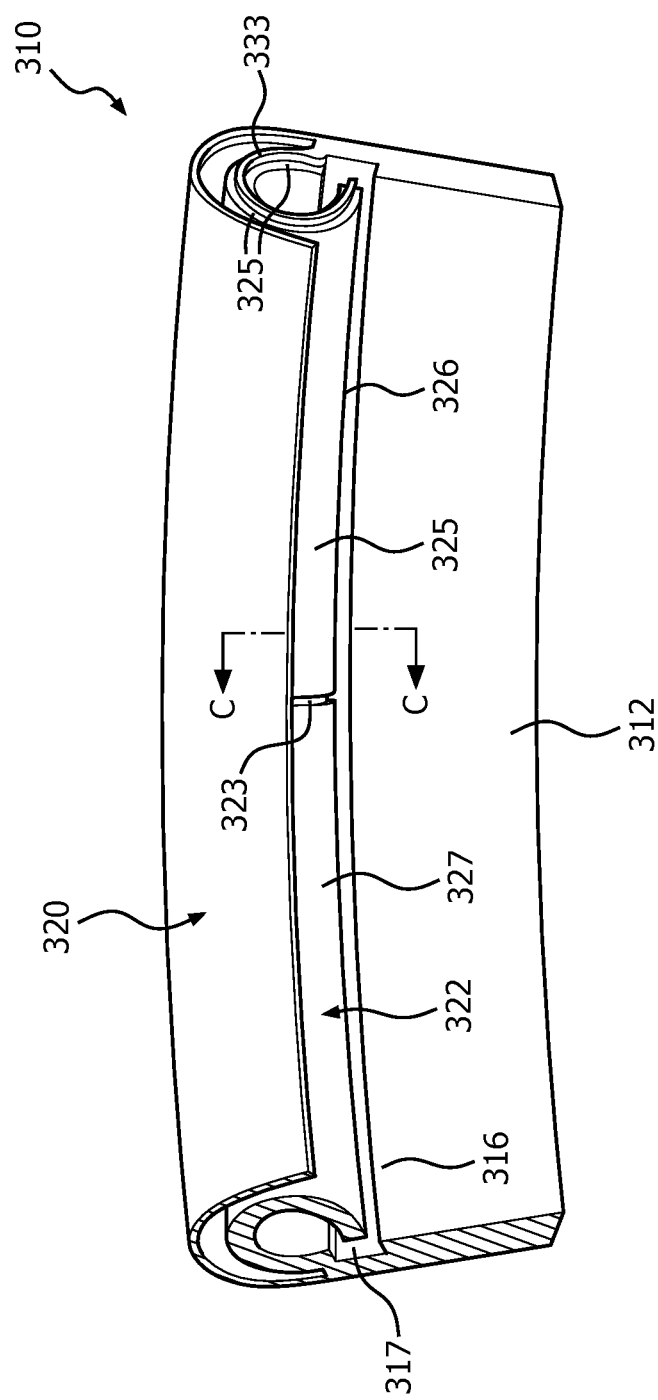
FIG. 7A is a section view of a portion of another cushion member, in accordance with another non-limiting embodiment of the disclosed concept.

FIG. 7A shows a section view of a portion of another cushion member 310 that may be substituted into pressure support system 2 (FIG. 1) in place of cushion member 10 (FIG. 1), in accordance with another non-limiting embodiment of the disclosed concept. For purposes of illustration, a portion of FIG. 7A is shown without section lines. Cushion member 310 includes a sealing portion 320 and a support portion 322 that each extend from a second end 316 of a body 312. Support portion 322 terminates at a distal end 326, and second end 316 has an annular-shaped groove 317. In one example embodiment, distal end 326 is engaged with groove 317 to provide substantially the same advantages as cushion members 10,110,210, discussed above. As shown in FIG. 6A, support portion 322 includes a first circumferential portion 323, a second circumferential portion 325 extending from first circumferential portion 323, and a third circumferential portion 327 extending from first circumferential portion 323 away from second circumferential portion 325. First, second, and third circumferential portions 323,325, 327 each extend radially inwardly from second end 316 into a corresponding passage of cushion member 310.

Figure 7B:
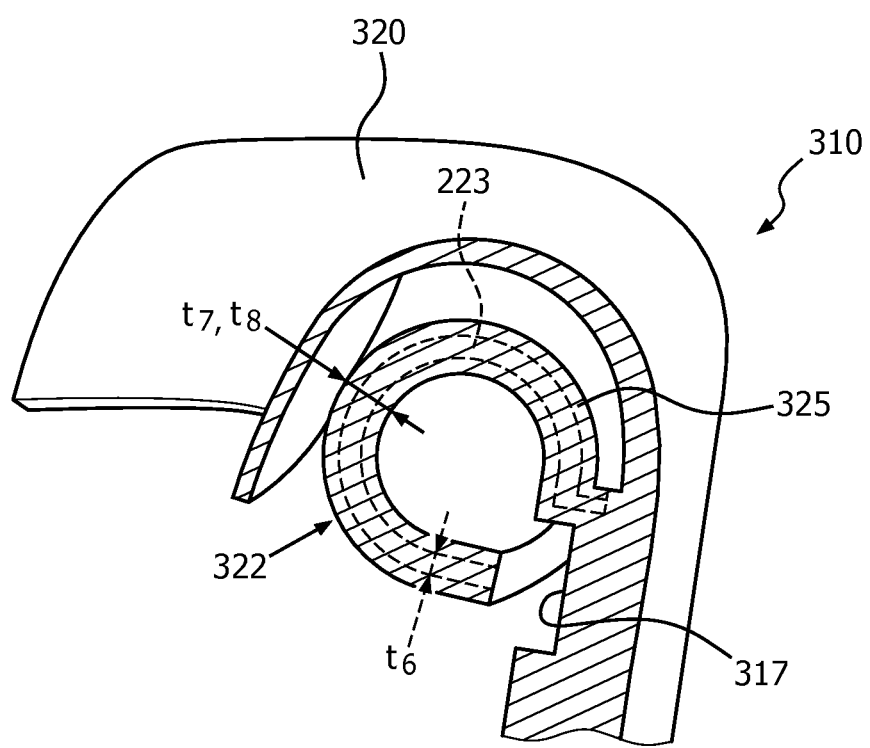
FIG. 7B is a section view of a portion of the cushion member of FIG. 7A, taken along line C-C of FIG. 7A.

As shown in FIG. 7B, first circumferential portion 323 (shown in hidden line drawing) has a first thickness $t_6$, second circumferential portion 325 has a second thickness $t_7$ greater than first thickness $t_6$, and third circumferential portion 327 (not indicated in FIG. 7B) has a third thickness $t_8$. In one embodiment, third thickness $t_8$ is generally the same as second thickness $t_7$. However, it will be appreciated that third thickness is need not be the same as second thickness $t_7$, without departing from the scope of the disclosed concept. That is, third thickness is can be any thickness with respect to second thickness $t_7$, as long as they are connected via first circumferential portion 323. Accordingly, first circumferential portion 323 provides a region in which support portion 322 can flex. That is, rather than support portion 322 potentially being constrained when sealing portion 320 is pressed into it by the face of a patient, as would be the case with a support portion having a constant thickness, support portion 322 is advantageously able to flex proximate first circumferential portion 323. For purposes of illustration, another transition zone is shown on the right side of FIG. 7A. As shown, support portion 322 further includes a fourth portion 333 extending from second circumferential portion 325. It will be appreciated that fourth portion 333 is thinned in a substantially similar manner as first circumferential portion 333, thereby allowing for the advantageous flexibility between second circumferential portion and another corresponding portion (not shown) adjacent fourth portion 333.

Accordingly, the disclosed concept provides for an improved (e.g., without limitation, better supported, better protected against redmarks, better able to deliver pressure support therapy) cushion member 10,110,210,310 and pressure support system 2 including the same.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination. [41] Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A cushion member for use in a pressure support system for delivering a flow of breathing gas to an airway of a patient, the cushion member comprising:
    an annular body comprising a first end and a second end disposed opposite the first end, the body defining a passage therethrough;
    a sealing portion extending from the second end of the body into the passage, the sealing portion having an outer surface structured to sealingly engage about the airway of the patient and an inner surface disposed opposite the outer surface; and
    a support portion extending from the second end of the body into the passage and terminating at a distal end, the support portion having an outer surface extending from the second end of the body to the distal end and an inner surface disposed opposite the outer surface, the distal end of the support portion engaging a portion of the body at or about the second end, wherein the portion of the body comprises a groove defined in the body, and wherein the distal end of the support portion is structured to interlock with the groove, wherein the entire inner surface of the sealing portion faces the outer surface of the support portion.

2. The cushion member according to claim 1, wherein, when the distal end of the support portion is engaged with the portion of the body, the support portion is generally tubular-shaped.

3. The cushion member according to claim 2, wherein, when the distal end of the support portion is engaged with the portion of the body, the inner surface of the sealing portion engages an outer surface of the support portion.

4. The cushion member according to claim 1, wherein the groove is annular-shaped.

5. The cushion member according to claim 1, wherein the support portion extends circumferentially about at least a portion of the passage; wherein the support portion has a first circumferential portion and a second circumferential portion; wherein the first circumferential portion has a first thickness; and wherein the second circumferential portion has a second thickness greater than the first thickness.

6. The cushion member according to claim 5, wherein the support portion further has a third circumferential portion; wherein the third circumferential portion has a third thickness ($t_8$) greater than the first thickness; and wherein the third thickness is generally the same as the second thickness.

7. The cushion member according to claim 5, wherein the support portion further has a third circumferential portion having a third thickness ($t_5$) greater than the second thickness and the first thickness.

8. The cushion member according to claim 5, wherein the first circumferential portion has a first outer surface; wherein the second circumferential portion has a second outer surface; and wherein the support portion further has a transition surface extending from and being disposed perpendicular to the first outer surface and the second outer surface such that the first outer surface is offset a distance (d) from the second outer surface.

9. The cushion member according to claim 1, wherein the support portion comprises a first support portion; wherein the cushion member further comprises a second support portion extending from the second end of the body into the passage; wherein the second support portion has a distal end structured to engage a portion of the body at or about the second end; and wherein the first support portion and the second support portion are spaced from and disposed adjacent one another.

10. A cushion member for use in a pressure support system for delivering a flow of breathing gas to an airway of a patient, the cushion member comprising:
  an annular body comprising a first end and a second end disposed opposite the first end, the body defining a passage therethrough;
  a sealing portion extending from the second end of the body into the passage, the sealing portion having an outer surface structured to sealingly engage about the airway of the patient and an inner surface disposed opposite the outer surface; and
  a support portion extending from the second end of the body into the passage and terminating at a distal end, the support portion having an outer surface extending from the second end of the body to the distal end and an inner surface disposed opposite the outer surface, the support portion being movable between a first position corresponding to disengagement between the distal end of the support portion and the body, and a second position corresponding to engagement between the distal end of the support portion and a portion of the body at or about the second end, wherein the portion of the body comprises a groove defined in the body, and wherein the distal end of the support portion is structured to interlock with the groove, wherein the entire inner surface of the sealing portion faces the outer surface of the support portion.

11. A pressure support system for delivering a flow of breathing gas to an airway of a patient, the pressure support system comprising:
  a gas flow generator;
  a conduit coupled to the gas flow generator; and
  a cushion member comprising:
    an annular body comprising a first end and a second end disposed opposite the first end, the body defining a passage therethrough, the first end being coupled to the conduit,
    a sealing portion extending from the second end of the body into the passage, the sealing portion having an outer surface structured to sealingly engage about the airway of the patient and an inner surface (disposed opposite the outer surface; and
    a support portion extending from the second end of the body into the passage and terminating at a distal end, the support portion having an outer surface extending from the second end of the body to the distal end and an inner surface disposed opposite the outer surface, the distal end of the support portion engaging a portion of the body at or about the second end, wherein the portion of the body comprises a groove defined in the body, and wherein the distal end of the support portion is structured to interlock with the groove, wherein the entire inner surface of the sealing portion faces the outer surface of the support portion.

12. The pressure support system according to claim 11, wherein, when the distal end of the support portion is engaged with the portion of the body, the support portion is generally tubular-shaped.

13. The pressure support system according to claim 12, wherein, when the distal end of the support portion is engaged with the portion of the body, the inner surface of the sealing portion engages an outer surface of the support portion.

* * * * *